(12) United States Patent
Maliglowka et al.

(10) Patent No.: US 8,048,099 B2
(45) Date of Patent: Nov. 1, 2011

(54) SURGICAL OBTURATOR

(75) Inventors: Johann Maliglowka, Kolbingen (DE); Rupert Mayenberger, Rielasingen (DE); Tom Schweitzer, Tuttlingen (DE)

(73) Assignee: Aesculap AG, Tuttlingen (DE)

( * ) Notice: Subject to any disclaimer, the term of this patent is extended or adjusted under 35 U.S.C. 154(b) by 318 days.

(21) Appl. No.: 12/290,452

(22) Filed: Oct. 29, 2008

(65) Prior Publication Data
US 2009/0118755 A1 May 7, 2009

Related U.S. Application Data

(63) Continuation of application No. PCT/EP2007/003882, filed on May 3, 2007.

(30) Foreign Application Priority Data

May 27, 2006 (DE) .......................... 10 2006 024 756

(51) Int. Cl.
*A61B 17/34* (2006.01)
(52) U.S. Cl. ........................................ 606/185; 606/172
(58) Field of Classification Search .......... 606/184–185; 604/164; 452/69; 27/21.1; 408/231, 233, 408/713
See application file for complete search history.

(56) References Cited

U.S. PATENT DOCUMENTS

| | | | |
|---|---|---|---|
| 3,051,132 A | 8/1962 | Johmann | |
| 5,066,288 A | 11/1991 | Deniega et al. | |
| 5,215,526 A | 6/1993 | Deniega et al. | |
| 5,324,268 A | 6/1994 | Yoon | |
| 5,342,382 A * | 8/1994 | Brinkerhoff et al. | 606/184 |
| 5,346,459 A | 9/1994 | Allen | |
| 5,360,405 A | 11/1994 | Yoon | |
| 5,423,770 A | 6/1995 | Yoon | |
| 5,462,532 A | 10/1995 | Gresl | |
| 5,569,289 A | 10/1996 | Yoon | |
| 5,591,191 A | 1/1997 | Kieturakis | |
| 5,609,604 A * | 3/1997 | Schwemberger et al. | 606/185 |
| 5,645,076 A | 7/1997 | Yoon | |
| 5,662,673 A * | 9/1997 | Kieturakis | 606/185 |
| 5,674,237 A | 10/1997 | Ott | |
| 5,676,156 A | 10/1997 | Yoon | |
| 5,755,697 A | 5/1998 | Jones et al. | |
| 5,779,680 A | 7/1998 | Yoon | |
| 5,807,402 A | 9/1998 | Yoon | |
| 2003/0100914 A1 | 5/2003 | O'Heeron et al. | |

FOREIGN PATENT DOCUMENTS

| | | |
|---|---|---|
| DE | 44 11 685 | 10/1995 |
| DE | 197 18 086 | 11/1998 |
| DE | 20 2006 008 405 | 7/2006 |
| DE | 20 2006 008 406 | 7/2006 |
| DE | 20 2006 018 883 | 2/2007 |
| EP | 0 135 364 | 3/1985 |
| EP | 0 495 633 | 7/1992 |
| EP | 0 499 457 | 8/1992 |

(Continued)

*Primary Examiner* — Tom Hughes
*Assistant Examiner* — Rachel S Papeika
(74) *Attorney, Agent, or Firm* — Lipsitz & McAllister, LLC

(57) ABSTRACT

To enable puncture of a body wall with a greater degree of sensitivity with a surgical obturator for puncturing the body wall having a knife, the cutting edge of which extends outwards from a tip of the obturator in the direction of various sides and backwards in relation to the tip, and which is orientated throughout its entire length parallel to the puncturing direction, so that the cutting edge points in the puncturing direction, it is proposed that the cutting edge be of helical line-shaped configuration.

3 Claims, 4 Drawing Sheets

FOREIGN PATENT DOCUMENTS

| | | |
|---|---|---|
| EP | 0 551 968 | 7/1993 |
| EP | 0 600 921 | 6/1994 |
| EP | 0 705 077 | 4/1996 |
| WO | 89/03661 | 5/1989 |

\* cited by examiner

SURGICAL OBTURATOR

This application is a continuation of international application number PCT/EP2007/003882 filed on May 3, 2007.

The present disclosure relates to the subject matter disclosed in international application number PCT/EP2007/003882 of May 3, 2007 and German application number 10 2006 024 756.6 of May 27, 2006, which are incorporated herein by reference in their entirety and for all purposes.

BACKGROUND OF THE INVENTION

The invention relates to a surgical obturator for puncturing a body wall with a knife, the cutting edge of which extends outwards from a tip of the obturator in the direction of various sides and backwards in relation to the tip, and which is orientated throughout its entire length parallel to the puncturing direction so that the cutting edge points in the puncturing direction.

Obturators of this kind are used to form an opening in a body wall, through which a cannula or tube can be inserted into the interior of the body, for example, to prepare for minimally invasive surgery.

Obturators with cutting edges pointing in the puncturing direction and extending outwards and backwards from the tip are known, in which the cutting edges of the knife have a V-shape, i.e., the straight-lined cutting edges are inclined in relation to a longitudinal axis of the obturator that runs through the obturator tip. Clean cuts can be made with such obturators when the obturator is advanced through the body wall, but it is difficult to perform this puncturing operation with such a degree of sensitivity that internal organs are not inadvertently injured after the puncturing. Once the cutting operation has been initiated, it progresses with relatively little resistance, so that the surgeon is unable to precisely determine the extent to which the obturator has already penetrated the body wall.

The object of the invention is to so construct a generic surgical obturator that with it puncturing of a body wall is possible with a greater degree of sensitivity.

SUMMARY OF THE INVENTION

This object is accomplished, in accordance with the invention, with a surgical obturator of the kind described at the outset in that the cutting edge is of helical line-shaped configuration. With such a configuration, the puncturing is performed not only by axially advancing the obturator but by superimposition of advancing motion and rotational motion similar to the motion when screwing-in a self-cutting bone screw. Such a superimposed advancing and rotational motion can be carried out in a considerably more controlled manner than a pure advancing motion, and the surgeon can also judge from the angle of rotation the extent to which the knife has already penetrated the body wall.

It is advantageous for the sections of the knife at various sides of the tip to be transferable into each other's position by rotation about a longitudinal axis passing through the tip of the obturator, i.e., for similar geometries of the sections of the knife to be used, which differ solely by their angular position.

In particular, it may be provided that the projection of the cutting edge onto a plane extending perpendicularly to the longitudinal axis of the obturator, starting from the tip, forms the arc of a circle or at least approximately the arc of a circle.

It is advantageous for the arc of the circle to extend from the tip over an angle of approximately 180°, i.e., approximately over a semicircle.

The sections of the cutting edges at various sides of the tip may merge without any sharp bend. In this case, the cutting edge extends in the region of the obturator tip transversely to the longitudinal axis of the obturator.

In another preferred embodiment, it is provided that the sections of the cutting edges at various sides of the tip merge at an acute angle, thereby producing a pointed arch-shaped configuration.

In a further embodiment, it may be provided that the sections of the cutting edges at various sides of the tip merge so as to form a centering tip which makes it easier for the surgeon to position the obturator.

It is expedient for the obturator to bear at one end thereof a tapering insertion area with a slot through which the knife projects. Thus, the knife is covered to a large extent by the insertion area, and only the cutting edges project slightly from the slot. The insertion area engages the tissue of the body wall when the obturator is screwed-in and advanced so as to puncture an opening therein. This enables good guidance and simultaneously closes the opening being made in the body wall, possibly even in a gas-tight manner.

The insertion area may, for example, be of approximately frustoconical configuration and have a rounded tip.

The following description of preferred embodiments of the invention serves in conjunction with the drawings for further explanation.

DETAILED DESCRIPTION OF THE INVENTION

Figure 1:
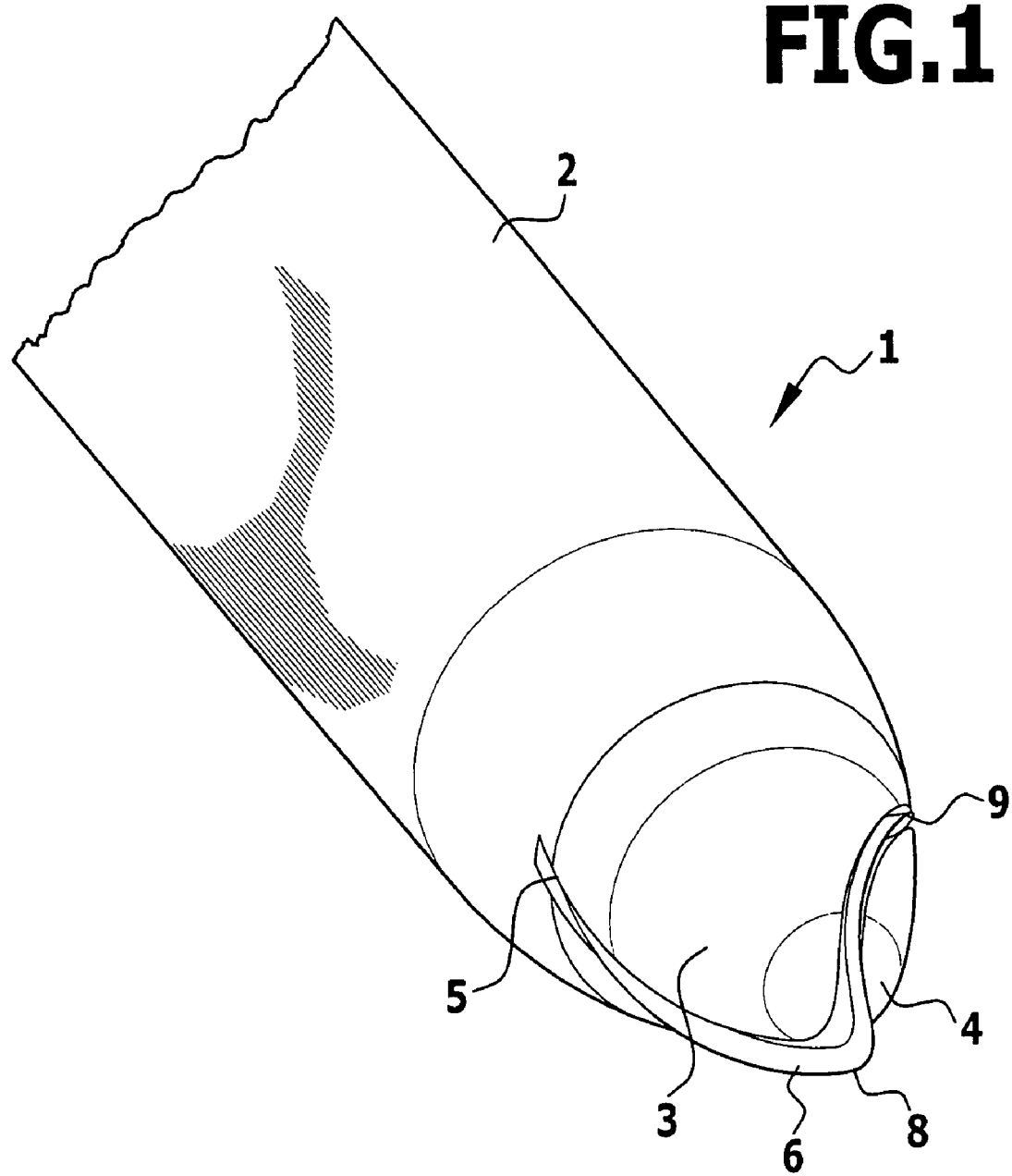
FIG. 1: a perspective view of the puncture area of an obturator with a helical cutting edge geometry.
Figure 2:
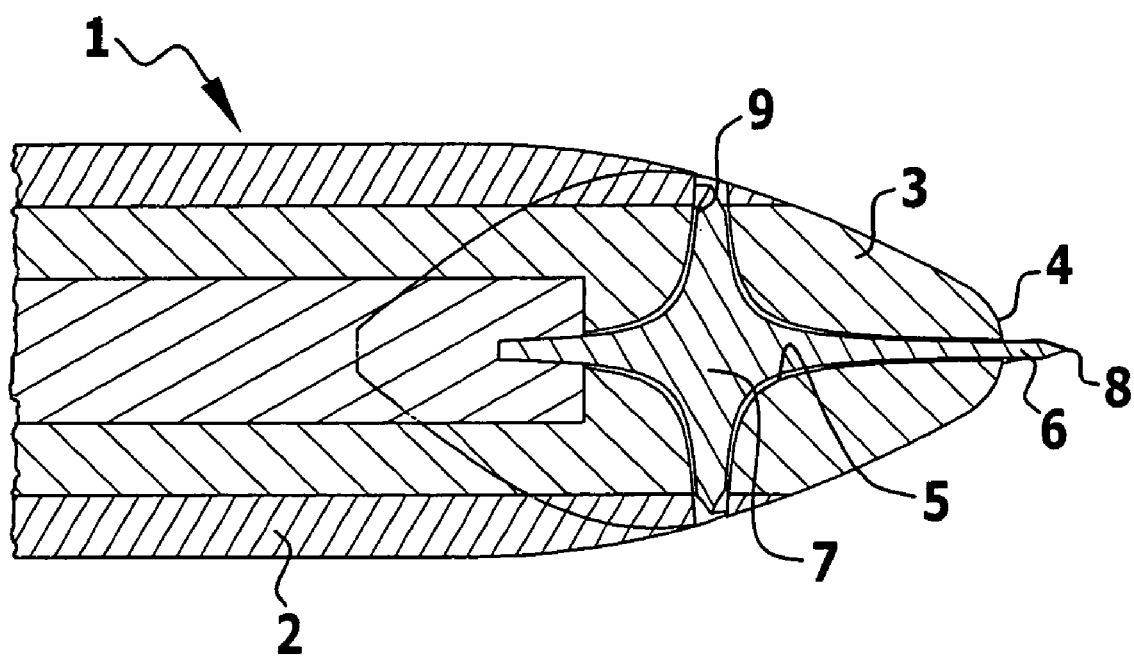
FIG. 2: a longitudinal sectional view through the puncture area of the obturator of FIG. 1 taken along line 2-2 in FIG. 3.

The obturator 1 represented in the drawings comprises a tubular shaft-shaped housing 2 with an approximately frustoconical insertion area 3 at one end, which leads continuously from the outer wall of the shaft-shaped housing 2 to a tip. This tip 4 is rounded.

Arranged in the insertion area 3 is a slot 5 which passes through the tip 4 and extends parallel to the longitudinal axis of the obturator 1.

Figure 4:
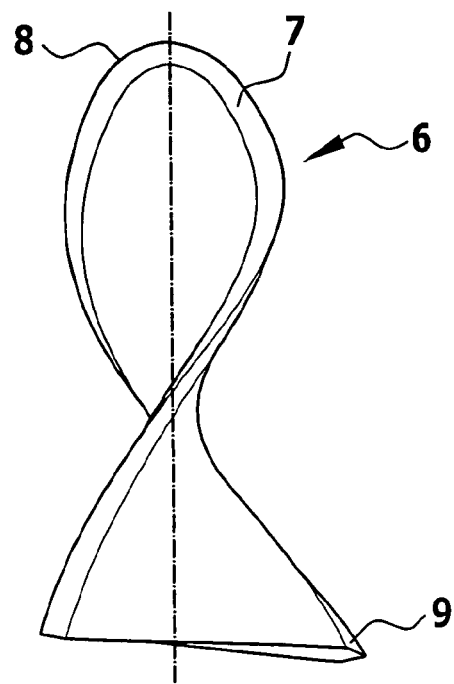
FIG. 4: a schematic representation of a knife for the obturator of FIGS. 1 to 3.

There extends through this slot 5 a knife 6 which is part of a knife body 7 which is arranged inside the housing 2 below the insertion area 3. As shown in FIG. 4, the knife body 7 is formed in the shape of a helix. The knife 6 projects slightly from the slot 5, and the cutting edge 8 of the knife 6 extends substantially parallel to the slot 5.

Figure 3:
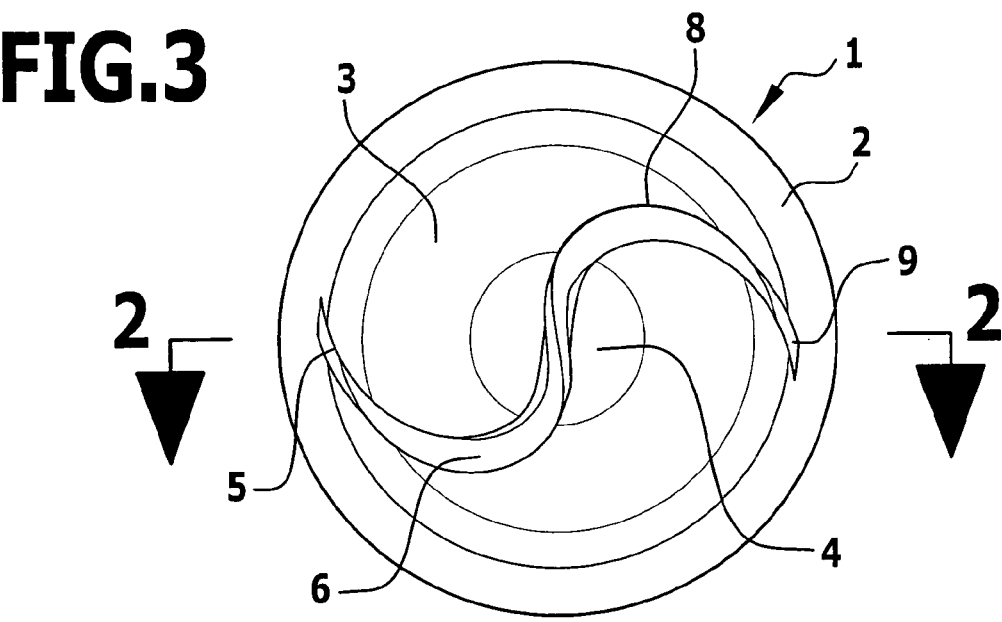
FIG. 3: a view of the obturator of FIG. 1 taken from the tip.

The cutting edge 8 extends helically, i.e., it extends outwards from the tip 4 on an expanding helical line towards the shaft-shaped housing 2. The projection of the helical line-shaped cutting edge 8 onto a plane extending perpendicularly to the longitudinal axis of the obturator is, therefore, S-shaped, as shown in FIG. 3. Starting from the tip 4 of the cutting edge, this projection is approximately a semicircle, but the end 9 that is remote from the tip 4 still terminates in the region of the insertion area 3, i.e., at a radial spacing from the tip 4 which is smaller than the radius of the shaft-shaped housing 2. The cutting edge 8 extends over approximately 180°, and the two sections of the cutting edge 8 on opposite sides of the tip 4 merge in the region of the tip 4 without any sharp bend, i.e., in the region of the tip 4, the cutting edge extends transversely to the longitudinal axis of the obturator. As shown in FIG. 3, the two sections of the cutting edge outside of the region of the tip are arranged on an outer convex side of the knife body 7.

The two sections of the cutting edge lying on opposite sides of the tip 4 are of identical construction, so that by rotating them through 180° around the longitudinal axis of the housing 2, these sections can be brought into congruence.

When this obturator 1 is moved in the direction of its longitudinal axis up to a body wall in which an opening is to be made, the cutting edge 8 in the region of the tip 4 first takes up its position on the outer side of the body wall and makes a horizontal incision therein. Upon advancing it further, the surgeon simultaneously rotates the obturator 1 about its longitudinal axis so that the spiral or helical cutting edge 8, similarly to a self-cutting bone screw with a screw thread diameter which increases in the screw-in direction, penetrates the body wall and continuously widens the cut which has been made until the cut has a length which is predetermined by the overall length of the cutting edge 8. The cutting operation has then reached completion, but the insertion area 3 has not yet passed fully through the opening that has been made as its outer diameter is larger at the housing end. The insertion area 3, therefore, seals the opening tight, and this opening can be widened by pressing the insertion area 3 further in. The tissue of the body wall then slides in a sealing manner along the insertion area 3 and lies against the housing 2.

Owing to the helical line-shaped configuration of the cutting edge 8, the obturator 1 must undergo rotational motion in addition to advancing motion in order to make the puncture, and this superimposed motion comprising advancing motion and rotational motion allows the surgeon to puncture the body wall with a considerably greater degree of sensitivity than with a cutting edge which is of straight-lined configuration and, therefore, allows only advancing motion of the obturator 1.

Figure 6:
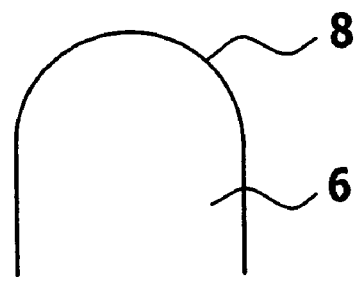

The sections of the cutting edge 8 on opposite sides of the tip 4 may merge in the described manner without any sharp bend, which, viewed from the side, then results in a contour as shown in FIG. 6.

Figure 5:
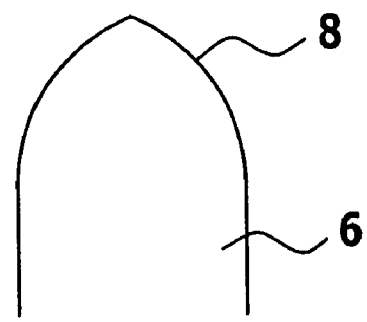
FIGS. 5 to 8: different configurations of the cutting edges in the region of the obturator tip.
Figure 7:
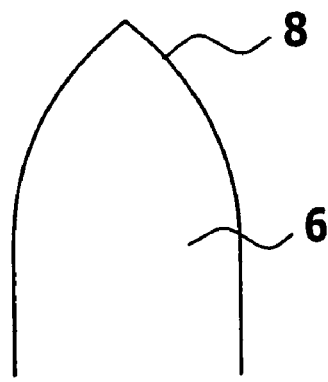

It may, however, also be provided that the sections of the cutting edge 8 meet at an acute angle at the tip 4, as shown in FIGS. 5 and 7.

Figure 8:
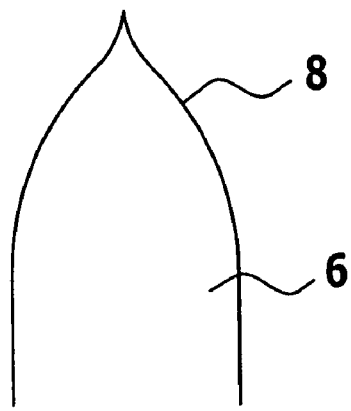

In a further preferred embodiment according to FIG. 8, it is provided that the two sections of the cutting edge 8 form in the region of the tip 4 a centering tip which makes it easier for the surgeon to position the obturator on the body wall.

The invention claimed is:

1. Surgical obturator for puncturing a body wall, comprising:
   a tubular housing with a distal tapering rounded frusto-conical insertion area with an s-shaped slot along a terminal distal end,
   a knife comprising a knife body formed in the shape of a helix and a cutting edge formed on the knife body,
   the cutting edge of the knife following the shape of the knife body and extending in the shape of a helical line outwards from a terminal tip of the obturator in the direction of opposite sides and backwards from the tip in two sections,
   a projection of the helical line-shaped cutting edge onto a plane extending perpendicularly to a longitudinal axis of the obturator being S-shaped,
   the two sections of the cutting edge at the opposite sides of the terminal tip merging without any sharp bend in a region of the terminal tip, so that in the region of the terminal tip the cutting edge is arranged in a center of the knife and extends transversely to the longitudinal axis of the obturator,
   the two sections of the cutting edge outside of the region of the terminal tip being arranged on an outer convex side of the knife body, and
   the two sections of the cutting edge at the opposite sides of the terminal tip being transferable into each other's position by rotation through 180° about the longitudinal axis of the obturator
   wherein the cutting edge of the knife body projects through the s-shaped slot of the insertion area of the housing.

2. Obturator in accordance with claim 1, wherein the projection of each of the two sections of the cutting edge onto the plane extending perpendicularly to the longitudinal axis of the obturator, starting from the tip, forms an arc of a circle.

3. Obturator in accordance with claim 2, wherein the arc of the circle extends from the tip over an angle of approximately 180°.

\* \* \* \* \*